United States Patent [19]

Bales et al.

[11] Patent Number: 5,176,702
[45] Date of Patent: Jan. 5, 1993

[54] RATCHET LOCKING MECHANISM FOR SURGICAL INSTRUMENTS

[75] Inventors: Thomas O. Bales, Coral Gables; Gregory J. Murphy, Sunrise; Frank A. Scarfone, Boca Raton; Charles R. Slater, Fort Lauderdale; Kevin W. Smith, Miami, all of Fla.

[73] Assignee: Symbiosis Corporation, Miami, Fla.

[21] Appl. No.: 833,840

[22] Filed: Feb. 7, 1992

Related U.S. Application Data

[63] Continuation-in-part of Ser. No. 680,392, Apr. 4, 1991, and a continuation-in-part of Ser. No. 780,014, Oct. 21, 1991.

[51] Int. Cl.⁵ .................. A61B 17/28; A61B 17/32
[52] U.S. Cl. .................. 606/208; 606/205; 606/208; 606/206; 128/751; 74/575; 74/577 R; 74/577 M; 74/587; 81/319; 81/320; 81/328
[58] Field of Search ........... 128/749, 751; 606/167, 606/170, 176, 205, 206, 207, 208; 74/575, 577, 577 M, 578; 81/318, 319, 320, 321, 322, 323, 324, 328, 415

[56] References Cited

U.S. PATENT DOCUMENTS

| 823,155 | 10/1905 | Booker | 81/319 |
|---|---|---|---|
| 1,052,482 | 2/1913 | Sturtevont | 81/319 |
| 1,094,536 | 4/1914 | Davis | 81/322 |
| 1,106,518 | 8/1914 | Malti | 81/323 |
| 3,433,093 | 10/1966 | Marti | 74/578 |
| 3,470,872 | 10/1969 | Grieshaber | 606/208 |
| 4,483,562 | 11/1984 | Schoolman | 606/174 |
| 4,896,661 | 1/1990 | Bogert et al. | 606/207 |
| 4,896,678 | 1/1990 | Ogawa | 606/170 |

FOREIGN PATENT DOCUMENTS

| 0115624 | 8/1984 | European Pat. Off. | 606/205 |
|---|---|---|---|
| 0568905 | 4/1924 | France | 606/208 |
| 0748047 | 6/1933 | France | 606/207 |
| 0065432 | 7/1913 | Switzerland | 128/28 |

*Primary Examiner*—Kyle L. Howell
*Assistant Examiner*—Scott R. Akers
*Attorney, Agent, or Firm*—David P. Gordon

[57] ABSTRACT

Releasable ratchet mechanism for medical instruments such as endoscopic instruments are disclosed. The ratchet mechanism includes: a leaf spring with a locking barb which is located on a handle of the medical instrument; a ratchet on a lever arm of the medical instrument which lever arm is pivotally engaged to the handle; and a latch on the handle of the medical instrument. The latch on the handle engages and resiliently deforms the leaf spring to cause engagement of the locking barb in a groove of the ratchet when the latch is in a first position. When in a second position, the latch releases the locking barb from the ratchet groove. Preferably, the locking barb has an extending edge surface on an axis which is substantially parallel to the pivoting axis of the handle and lever arm, and the teeth of the ratchet have extending edge surfaces on axes substantially parallel to the extending edge surface of the locking barb. Also, preferably, the edge surfaces of said teeth of the ratchet are located along an arc of a cylinder having the handle/lever arm pivot axis as its center line.

34 Claims, 11 Drawing Sheets

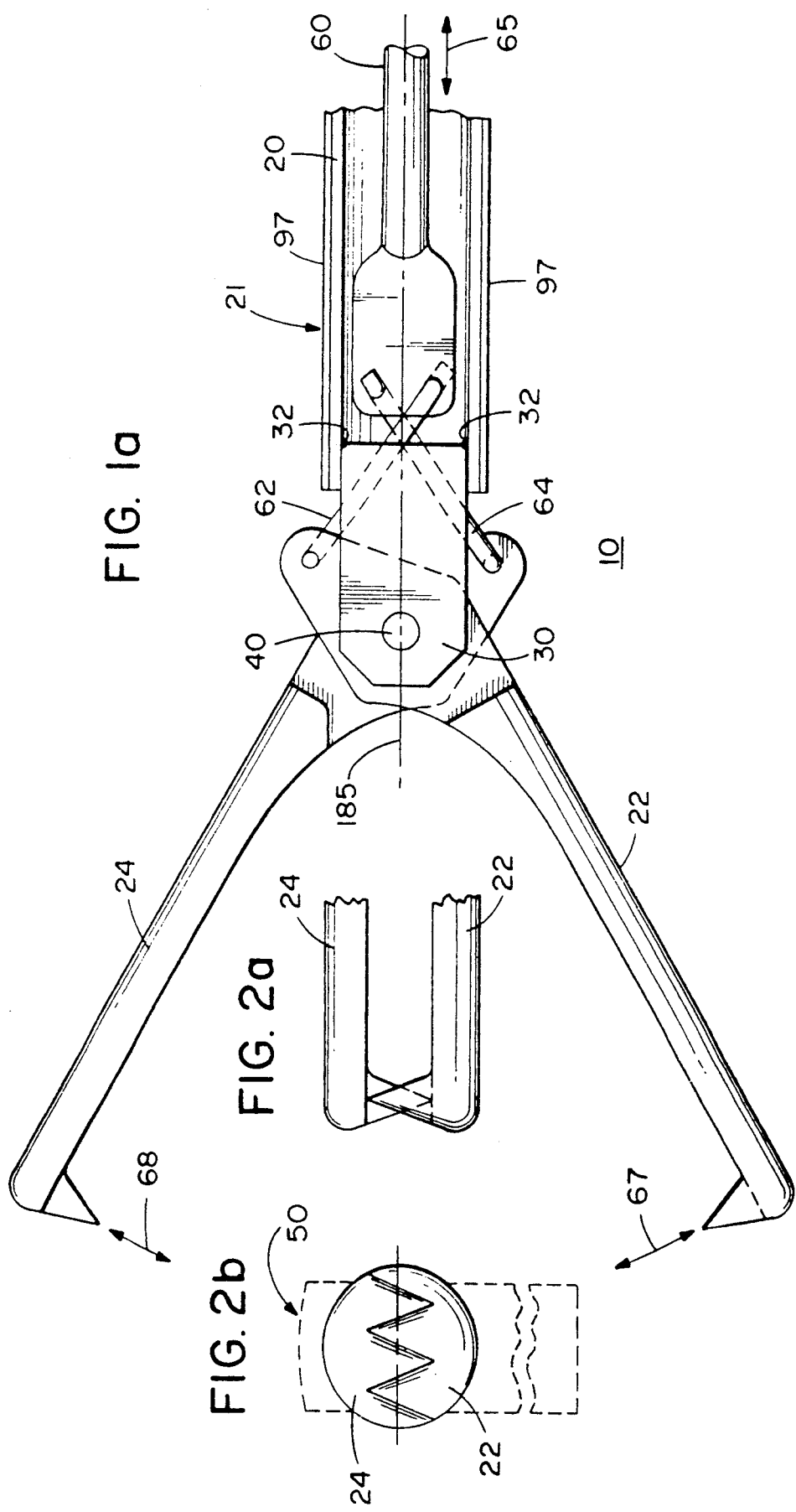

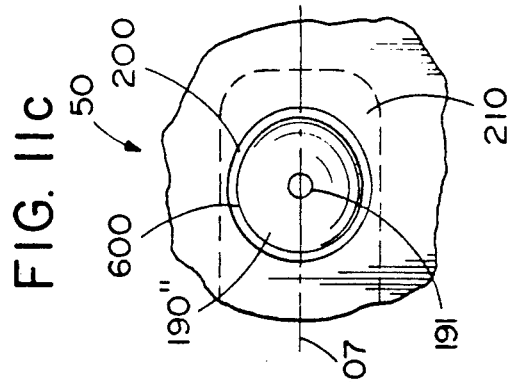
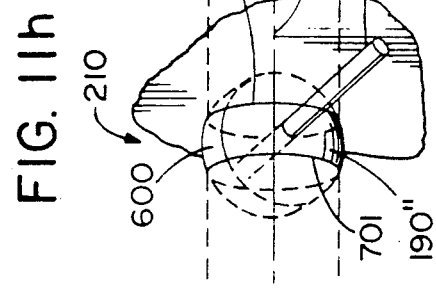
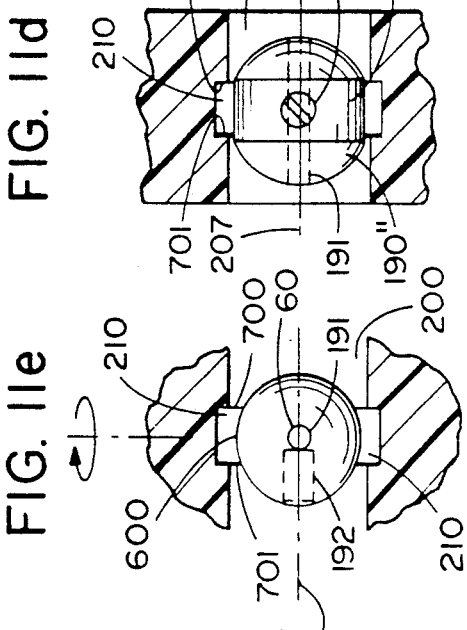
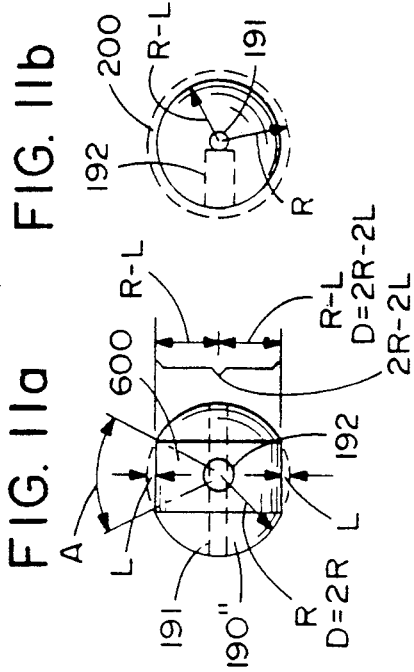
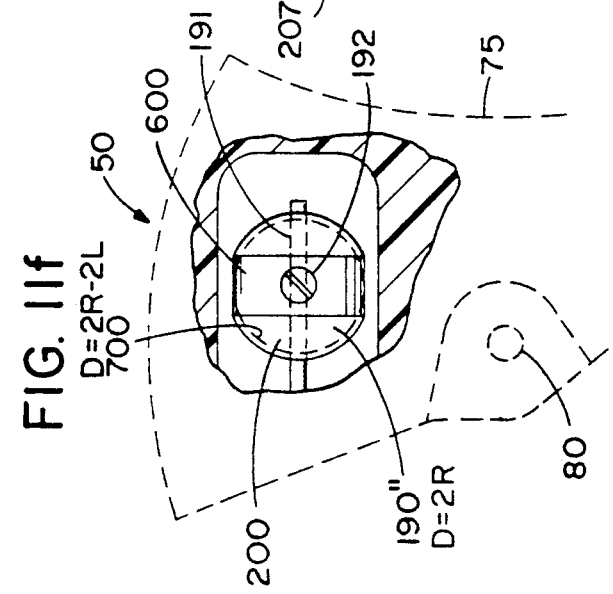
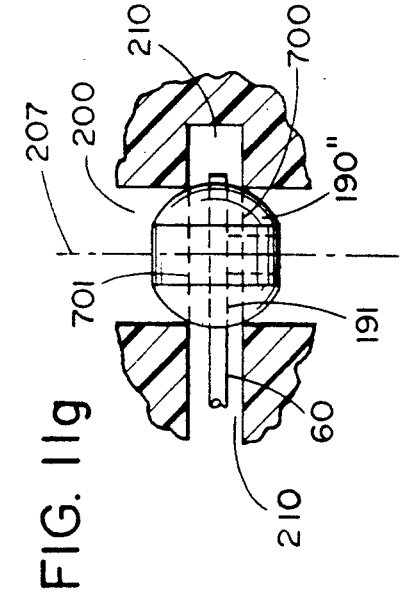

RATCHET LOCKING MECHANISM FOR SURGICAL INSTRUMENTS

This is a-continuation-in-part of U.S. Ser. Nos. 07/680,392, filed Apr. 4, 1991, and U.S. Ser. No. 07/780,014, filed Oct. 21, 1991, which are hereby incorporated by reference herein in their entireties.

BACKGROUND OF THE INVENTION

The present invention broadly relates to endoscopic surgical instruments. More particularly, the invention relates to disposable endoscopic instruments having end effectors and actuation means for effecting movement of the end effectors where the actuating means include apparatus for the locking of and fixed stepped movement of the end effectors relative to each other.

The endoscopy and laparoscopy procedures have recently become widely practiced surgical procedures. The endoscopy and laparoscopy procedures involve incising through body walls (e.g., such as the abdominal wall) for examining, viewing and/or operating on the ovaries, uterus, gall bladder, bowels, appendix, etc. Typically, trocars are utilized for creating the incisions. Trocar tubes are left in place in the abdominal wall so that the endoscopic or laparoscopic surgical tools may be inserted through the tube. A camera or magnifying lens is often inserted through a relatively large diameter trocar tube (e.g. 10 mm diameter) which for the laparoscopy procedure is generally located at the navel incision, while a cutter, dissector, extractor, or other surgical instrument is inserted through a typically smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

During a laparoscopic or endoscopic procedure, in order to properly grasp, clamp, or cut tissue or an organ, it is sometimes desirable to lock the end effectors of the endoscopic/laparoscopic tool in position relative to each other. Further, it is sometime desirable to effect movement of the end effectors toward each other in fine, stepped movements. In order to accomplish locking and stepped movement, the tools of the prior art have provided mating teeth and grooves on both the handle and lever of the tool such that movement of the teeth of the lever past the teeth of the handle effect a locking and stepping arrangement. However, such arrangements of the prior art have typically limited the practitioner to a situation where locking and stepping is the norm and torsional force is required to unlock the handle from the lever so as to release the end effectors. In addition, where disposable tools using plastic handles and levers are desirable, the double teeth and groove arrangement has proved to be unwieldy and generally unsatisfactory.

The endoscopic and laparoscopic tools of the prior art are primarily reusable stainless steel tools. Between each use of a stainless steel tool, the tool must be soaked, scrubbed, and disinfected. The usual procedure is then to dry the tool, wrap it, and put it in a steam autoclave. The tool is kept sterile until just prior to use when it is removed from the autoclave and unwrapped in the locale of the sterile field of use.

While reusable endoscopic and laparoscopic tools have functioned well for their intended purpose, the process of sterilizing the tool is problematic. Small pieces of tissue or organ often become lodged in the end effectors, and much labor is required to ensure that complete sterility is obtained and maintained. In addition, over time, sharp instruments such as a scissors get dull and must be discarded. However, prior to use of a particular instrument, the surgeon is not able to discern the state of the instrument and whether the instrument will satisfy the surgeon's requirements.

The alternative to reusable endoscopic and laparoscopic surgical tools are disposable tools. However, the complicated construction of endoscopic and laparoscopic surgical tools has typically dictated that the tools be expensive.

SUMMARY OF THE INVENTION

It is therefore an object of the invention to provide a well designed surgical instrument having an effective locking, stepping ratchet mechanism on the handle and lever.

It is a further object of the invention to provide disposable endoscopic and laparoscopic surgical instruments which provides a locking, stepping ratchet mechanism for extremely fine adjustment of the end effectors.

It is another object of the invention to provide surgical instruments of inexpensive design where a latch is provided to place the instrument in a locking, stepping mode, or to release the locked ratchet mechanism and permit free unstepped movement of the end effectors relative to each other.

In accord with the objects of the invention, medical instruments are provided such as for insertion through a trocar tube and generally comprise a longitudinally extending tube, a push rod which extends through the tube, an actuating apparatus engaging the tube and the push rod and imparting reciprocal axial motion to the push rod relative to the tube, end effector means coupled to the push rod by linkage means, and a clevis coupled to the tube at its proximal end and to the end effector means at its distal end, wherein axial movement of the push rod effects pivoting movement of the end effector means. Plastic shrink wrap is preferably utilized to electrically insulate the disposable instrument and extends over the aluminum tube and over at least a adjacent portion of the clevis. In accord with the present invention, the actuating apparatus in provided with a ratchet mechanism for adjustably holding the end effectors in a plurality of predetermined positions. The ratchet mechanism includes a resilient member, suitably in the form of a metal strip, attached at a first end, i.e. cantilevered, to either the handle means or the lever arm of the actuating apparatus, with the second end of the resilient member having a locking element for engagement with one of a tandem array of teeth positioned on an elongate member which extends from the other of said handle member or lever arm. A cammed latching means is provided adjacent the cantilevered end of the resilient strip to resiliently displace the resilient strip so as to engage the locking element of the resilient strip with the teeth Because the teeth and locking element are angled, activation of the cammed latching means permits movement of the lever arm towards the handle, but does not permit movement of the lever arm away from the handle. Release of the latching means permits disengagement.

In accord with another aspect of the invention, the actuating apparatus of the invention can be rotated about the longitudinal axis of the instrument relative to the end effector thus enhancing the usefulness of the instrument in surgical procedures. The actuating apparatus of the invention includes a sleeve (ferrule) means, a handle means and a lever arm.

The sleeve means of the actuating apparatus surrounds a proximal portion of the tube, is movable along the longitudinal axis of the tube, but is restrained from rotating about the longitudinal axis of the tube. The handle means surrounds the proximal end of the tube. The lever arm is pivotally engaged to the handle means and is also positioned at the proximal end portion of the tube. The sleeve means (at its proximal end) and the handle means (at its distal end) have opposing rim portions with respective mating surface configurations. The sleeve means is resiliently held in mating engagement with the handle means by a resilient means coupled to the sleeve and to the tube. When it is desired to change the rotational orientation of the end effector means relative to the actuating apparatus, the sleeve member is moved axially along the tube away from the handle member, against the restraining force exerted by the resilient means. Such movement disengages the mating portions of the sleeve and the handle member and leaves the sleeve free to rotate with the metal tube, the clevis means, and the end effectors relative to the handle means and the lever arm. With the provided arrangement, three hundred sixty degree rotation is available, and the resolution to which rotation may be obtained is only limited by the resolution of the mating portions of the sleeve and handle; i.e., the finer the teeth and grooves of each, the finer the resolution.

Because the metal tube, clevis and end effectors are free to rotate relative to the handle means and the lever arm, a rotating push rod engaging element is provided in the lever arm to couple the lever arm and the push rod. The rotating push rod engaging element is preferably generally spherical with a hole along a first axis for the push rod, and a hole along a second perpendicular axis for a set screw. The rotating push rod engaging element sits in a recess of the lever arm and rotates with the push rod, the outer tube, the end effectors, etc., when they are rotated relative to the handle means and the lever arm.

In another embodiment of the invention, in order to permit rotation of the end effectors relative to the handle means and lever arm, the outer metal tube is provided with a plurality of recesses or indents at its proximal end, and the actuating apparatus is provided with an electrode which is mounted in the handle, with one end protruding therefrom, and with the other end in contact with a metal resilient member which forcibly holds an engaged electrical contact element in engagement with the recesses or indents of the metal tube. With this arrangement, predetermined incremental relative rotation of the handle means and ever arm can be achieved and maintained by movement of the electrical contact to successive peripheral recesses upon rotation of the handle and ever arm.

Additional objects and advantages of the invention will become apparent to those skilled in the art upon reference to the detailed description taken in conjunction with the provided figures.

BRIEF DESCRIPTION OF THE DRAWINGS

FIGS. 1a and 1b are side elevation views which together show an instrument incorporating embodiments of the present invention;

FIGS. 2a and 2b are side and front elevation views showing the end effectors of FIG. 1a in a closed position;

FIG. 9b is a cross sectional view illustrating the electrical contact arrangement for the instrument of FIG. 9a;

FIG. 10-1 is a diagram defining particular angles of a portion of the ratchet mechanism;

FIG. 10d schematically shows various positions for the end effectors of FIG. 1a;

FIGS. 11a and 11b are respectively a front elevation view and a side view of an alternative push rod engaging element of the invention;

FIGS. 11c and 11d are respectively a partial side elevation view and a cross-sectional view of the lever arm of the invention with the push rod engaging element of FIG. 11a in an insertion position:

FIGS. 11e, 11f, and 11g are respectively a cross-sectional view, a partial side elevation view, and partial top plan view of the lever arm of the invention with the push rod engaging element of FIG. 11a in an rod engaging position; and FIG. 11h is a partial perspective view of the push rod engaging element of FIG. 11a in a rod engaging position.

DETAILED DESCRIPTION OF INVENTION

Figure 1B:
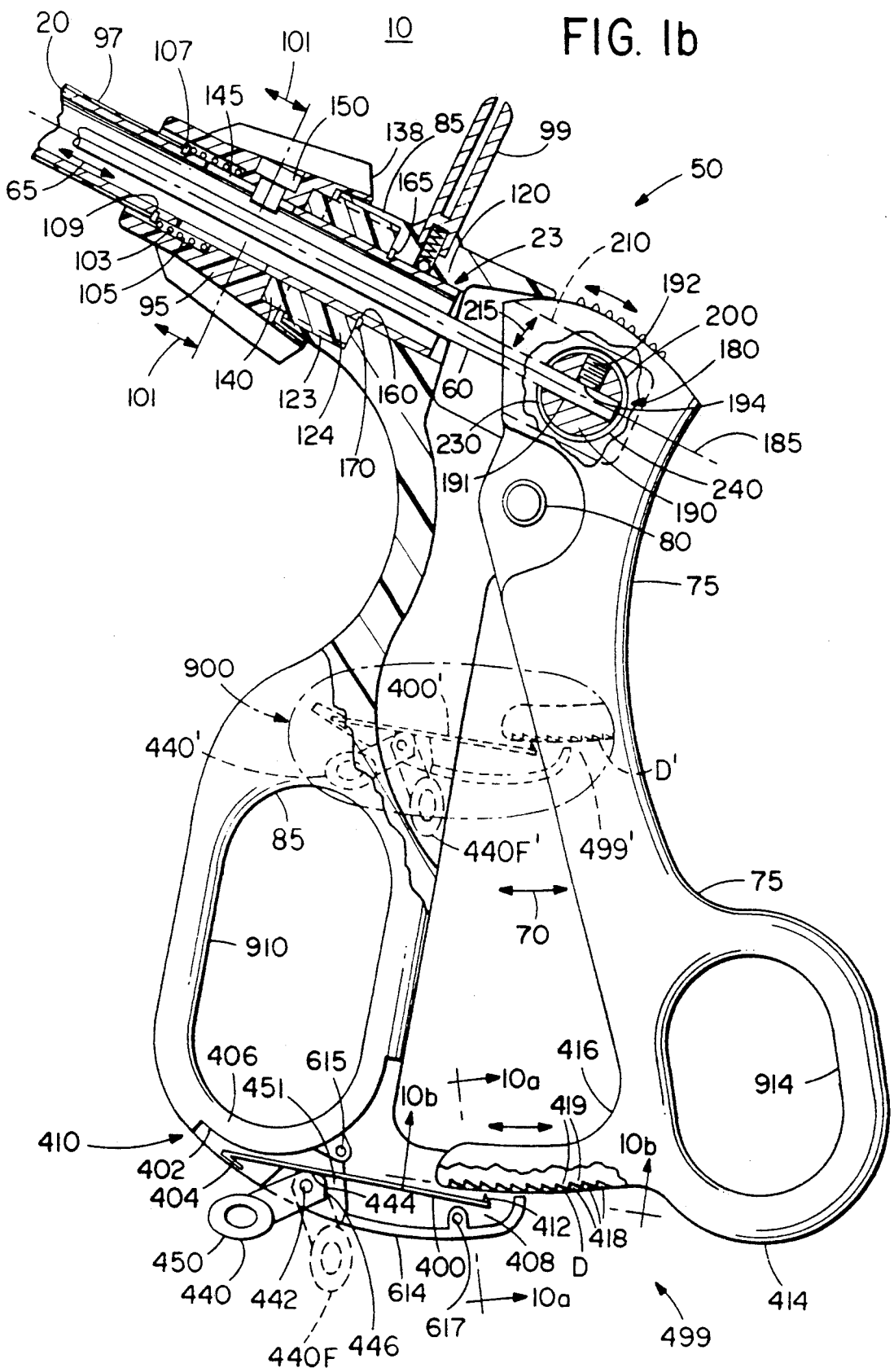

With reference to FIGS. 1a and 1b, a disposable endoscopic or laparoscopic surgical instrument is indicated at 10. The disposable surgical instrument 10 broadly comprises an aluminum tube 20 having a longitudinal axis 185, end effectors 22, 24, a clevis means 30, actuating apparatus 50, and a push rod 60. The clevis means 30 is advantageously a separately formed aluminum piece which fixedly engages aluminum tube 20 at the distal end 21 of the aluminum tube, e.g., by crimping of tube 20 as indicated a 32. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site. The clevis 30 also engages the end effectors 22, 24 at pivot pin or screw 40, as the end effectors pivot around the pivot pin 40. The end effectors are also coupled at their proximal ends to the distal end of push rod 60 via coupling elements 62, 64. As is discussed more fully in the parent applications hereto, the clevis effectively translates the reciprocal motion (shown as 65) of the push rod 60 into the end effector means action indicated at 67, 68. Also, as discussed more fully in the parent applications hereto, metal tube 20 is provided with an insulating plastic shrink wrap layer 97 which provides protection when electrical energy is applied at terminal 99, e.g. for cauterization procedures.

As seen in FIGS. 1a, 2a and 2b, end effector elements 22, 24 are of the grasper type. However, it will be appreciated that the invention applies to any single or double acting instruments which are intended for insertion through a trocar tube. Thus, different types of end effectors can be utilized. In fact, different embodiments of the coupling elements, the clevis means, and the push rod as described in the parent applications hereto may be utilized in conjunction with the preferred aspects of the present invention. Regardless, FIG. 2a shows end effectors 22, 24 in a closed position and FIG. 2b is a front elevation view of the configuration of FIG. 2a showing the actuating mechanism 50 (in phantom) which is more fully illustrated in FIG. 1b and described hereinbelow.

As aforementioned, the reciprocal movement of push rod 60 back and forth, as indicated at 65 in FIG. 1a, imparts pivoting or rotational motion to end effectors 22, 24 as indicated at 67, 68. With reference to FIG. 1b, the reciprocal motion 65 of push rod 60 is effected by the lever action motion 70 of lever arm 75, of the actuating apparatus 50, which is pivotally engaged by means of pivot rod 80 to handle member 85. Handle member 85 and lever arm 75 are configured for one-hand operation as shown.

With most previous endoscopic instruments of the art, the orientation of the actuating apparatus 50, i.e. handle 85 and lever arm 75, with respect to end effectors 22, 24 was fixed. That is, if a surgeon desired to rotate the handle and lever arm to a more convenient position, the end effectors 22, 24 would also be rotated correspondingly. With the present invention, the actuating apparatus 50 can be rotated to any convenient orientation, and back and forth, through 360°, without causing any rotational movement of the end effectors 22, 24.

The details of the actuating apparatus which permit rotation according to a first preferred embodiment are more fully understood with reference to FIGS. 1b, 3, 4a, 4b, 5a, 5b, and 6. The actuating apparatus generally comprises a sleeve (ferrule) member 90, the handle means 85 and the lever arm 75. The sleeve member 90 surrounds a portion of metal tube 20 which is remote from the end effectors 22, 24, and which is just forwardly adjacent the proximal end 23 of metal tube 20. As shown by a comparison of FIGS. 1b and 3, sleeve member 90 is movable axially back and forth along metal tube 20 as indicated at 101 of FIG. 3. However, sleeve member 90 is restrained in its movement by a resilient spring or biasing means 103. Resilient spring 103 is shown as a coil spring peripherally surrounding metal tube 20 and seated in an inner peripheral slot or undercut section 105 of sleeve 90. The resilient spring 103 is held in compression by a retaining ring 107 and an inwardly projecting portion 95 of the sleeve member 90. The retaining ring 107 is seated in peripheral slot 109 of metal tube 20. Alternatively, the retaining ring 107 can be fixedly engaged to the metal tube 20 in the absence of such a peripheral slot. With the provided arrangement, sleeve 90 is coupled by resilient spring 103 to hollow tube 20 and is urged thereby toward the proximal end 23 of the metal tube 20.

Figure 6:
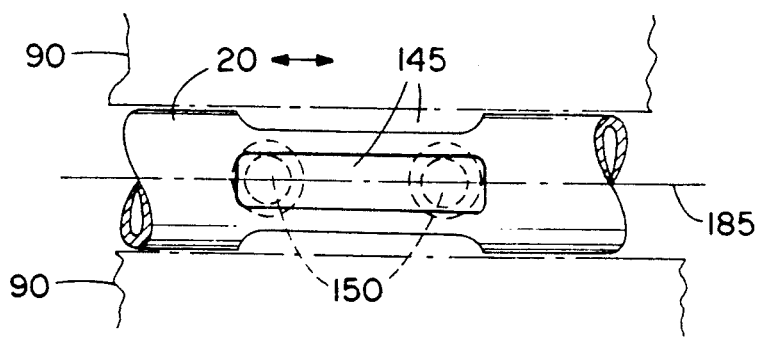
FIG. 6 is a side elevation view of a portion of a metal tube member of the instrument shown in FIG. 1b.

As shown in FIG. 1b and more particularly in FIG. 6, metal tube 20 is preferably provided with a plurality of axially extending peripherally spaced apart disposed slots 145 (although only one such slot is required) in a portion of the tube 20 surrounded by sleeve 90. One or more guide rods or inwardly extending protrusion 150 are seated in sleeve 90 and extend therethrough to slideably engage the axial slots 145. With the aforedescribed mating engagement (indicated as 140), sleeve 90 is restrained from rotation about metal tube 20, but is movable axially as indicated at 101 in FIG. 1b and FIG. 3.

Figure 4A:
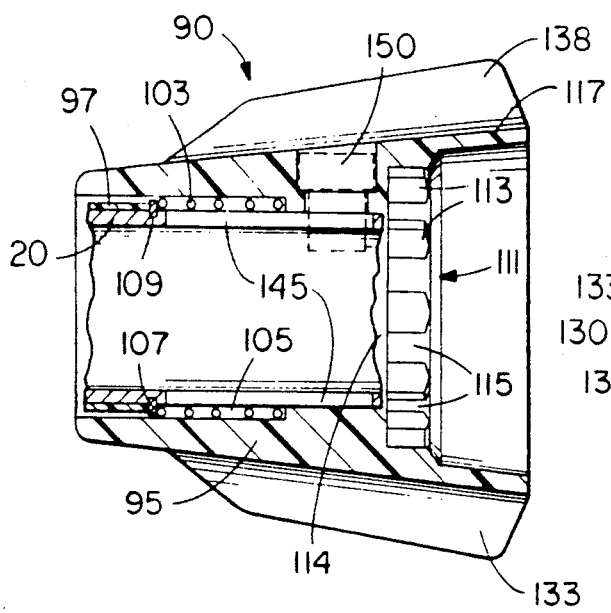
FIGS. 4a and 4b are side elevation and front elevation views of a sleeve element shown in FIG. 1b.
Figure 4B:
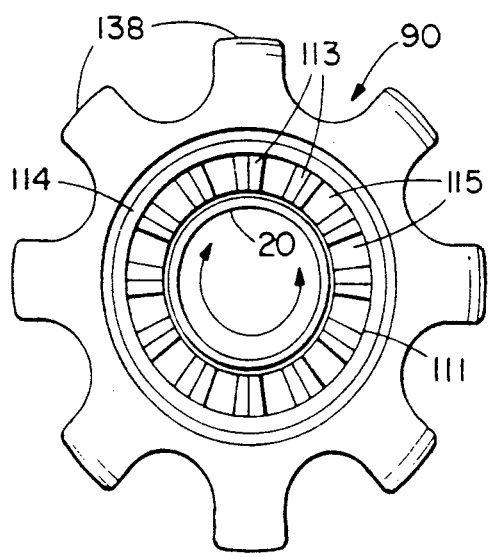

Turning to FIGS. 4a and 4b, it is seen that sleeve 90 has an engagement configuration 111 in the form of an integral peripheral proximal rim 114 of toothlike elements 113 and slots 115. The engagement configuration 111 is preferably enclosed by a flange portion 117 of sleeve 90 which extends around toothlike elements 113 and slots 115. Flange portion 117 preferably includes a series of ribs 138 which are circumferentially placed around the sleeve 90, which run in a manner substantially parallel the longitudinal axis of the surgical instrument, and which permit easy manipulation with the forefinger of the practitioner. As seen in FIG. 4a, the ribs 138 preferably taper downward as they extend toward the distal end of the sleeve 90.

Figure 5A:
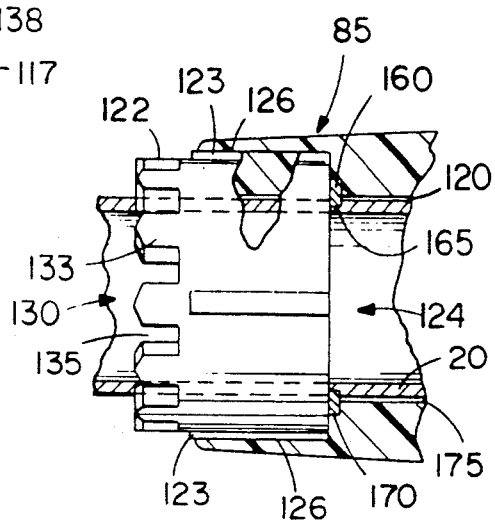
FIGS. 5a and 5b are side elevation and front elevation views of a portion of the handle of the instrument of FIG. 1b.
Figure 5B:
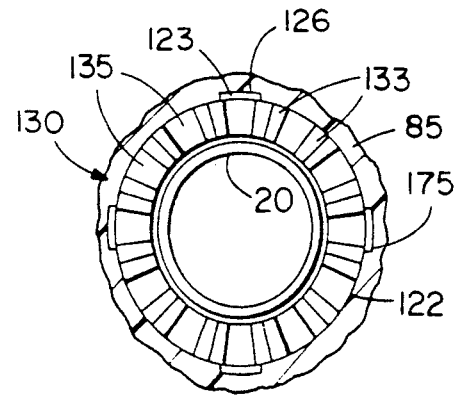

With reference to FIGS. 1b, 5a, and 5b, handle member 85 has a hollow distal portion 120 in the form of a bore coaxial with metal tube 20. Attached internally to the distal portion of handle 85 is a ring 124 which extends loosely around the tube 20. Ring 124 has a peripheral outer surface portion 122, (shown in FIGS. 5a and 5b) having integral ribs 123 which engage and are preferably sealed (e.g., by gluing) in slots 126 of hollowbore portion 120 of handle 85. Thus, ring 124 is fixed relative to the handle 85. In order to prevent handle 85 from sliding off the proximal end of tube 20, a retaining ring 160 is provided. Retaining ring 160 is seated in slot 165 of metal tube 20 and sits adjacent the proximal end of ring 124 (and in slot 170 of handle member 85 as shown best in FIG. 9). As aforementioned, metal tube 20 is free to rotate in ring 124 as it is only slideably engaged therewith and slightly spaced therefrom as indicated at 175.

Figure 3:
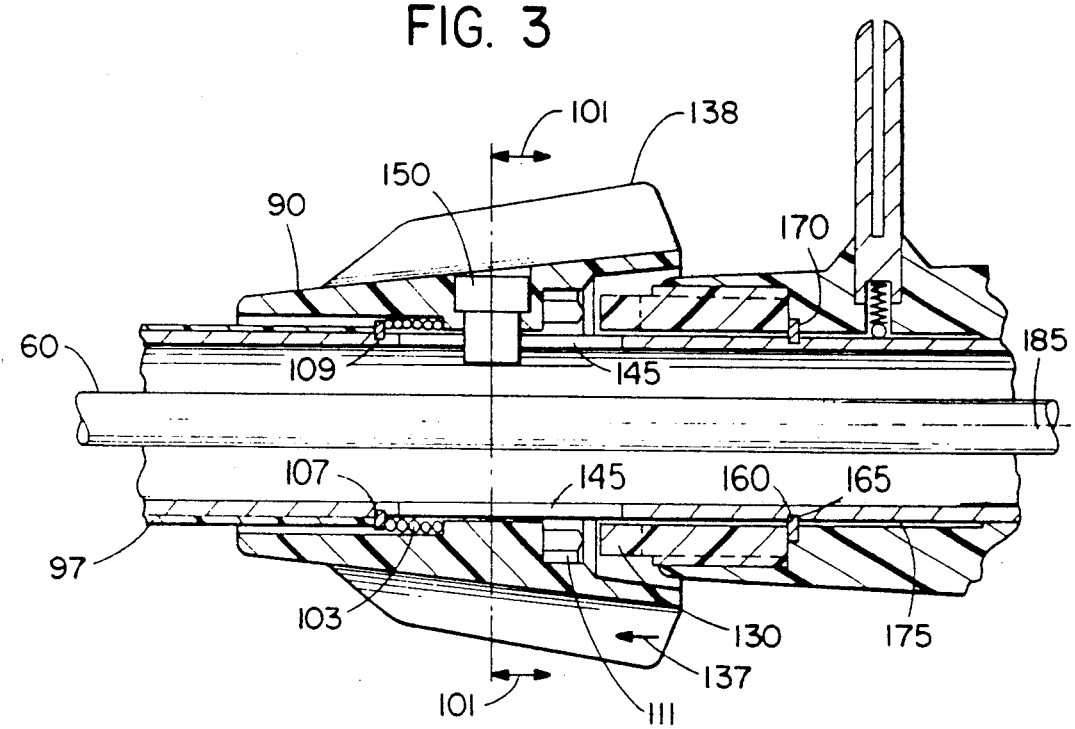
FIG. 3 is a side elevation partially in section of a portion of FIG. 1b showing certain operating elements in a disengaged position where the end effectors of FIG. 1a can be rotated relative to the handle and lever of FIG. 1b.

Ring 124 of handle member 85 has an engagement configuration 130 corresponding to engagement configuration 111 of sleeve 90 in the form of toothlike elements 133 and slots 135. In the "at-rest" position, toothlike elements 133 and slots 135 matingly engage (as indicated at 140 in FIG. 1b) the teeth 113 and slots 115 of sleeve 90 due to the force exerted by resilient coil spring 103 on sleeve 90 toward the proximal end 23 of metal tube 20. On the other hand, when, as shown in FIG. 3, a force 137 is applied to the outward radially extending ribs 138 of sleeve 90, the teeth 113 and slots 115 are disengaged from the teeth 133 and slots 135 of the handle member 85. With the disengaged condition illustrated in FIG. 3, metal tube 20 which is slidably engaged with the handle member 85 is free to rotate relative to the handle member.

Figure 7:
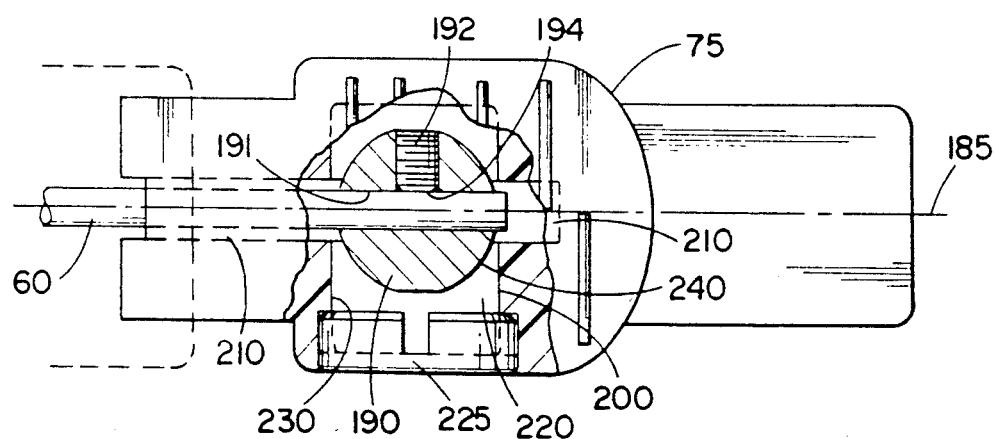
FIG. 7 is a partial plan view of a first embodiment of a portion of the instrument shown in FIG. 1b and showing a first

To enable the rotation of the metal tube 20, end effectors 22, 24, clevis means 30, sleeve 90, etc. with respect to the level arm 75 and handle 85, some mechanism for permitting rotation of the push rod 60 which is coupled at its proximal portion 180 to the lever arm 75 is required. With reference to FIG. 1b and FIG. 7 a first embodiment of a push rod coupling means is shown for accomplishing the relative rotation. In particular, the push rod coupling means is shown as a generally spherically surfaced element 190. Spherical element 190 is coaxial to push rod 60 and includes a diametrically located bore 191 through which push rod 60 extends. Push rod 60 is coupled to the spherical element 190 suitably by means of a recessed set screw 192 which threadably engages spherically surfaced element 190 and bears against and frictionally engages push rod 60 at 194.

In order to accommodate a spherical push rod coupling element, the lever arm 75 is provided with a cylindrical bore 200. Bore 200 is parallel to pivot rod 80 which engages the handle member 85 to the lever arm 75, and is transverse to the push rod 60 and the longitudinal axis 185 of metal tube 20. Cylindrical bore 200 has a diameter just slightly larger than that of element 190 and closely encloses spherically surface element 190.

As seen in FIG. 7, a slot 210 is provided in lever arm 75. Slot 210 transversely intersects the cylindrical bore 200 and receives push rod 60. The slot 210 is dimensioned to accommodate the displacement indicated at 215 of push rod 60 during movement of lever arm 75 and the spherically surfaced element 190. The bore 200 in lever arm 75 is suitably open at least on one side of the lever arm 75 as indicated at 220 to facilitate assembly and engagement of the push rod 60 with spherically surfaced element 190. A closely fitting cap 225 is preferably provided to close the bore and closely secure the spherical element 190 therein.

Figure 8:
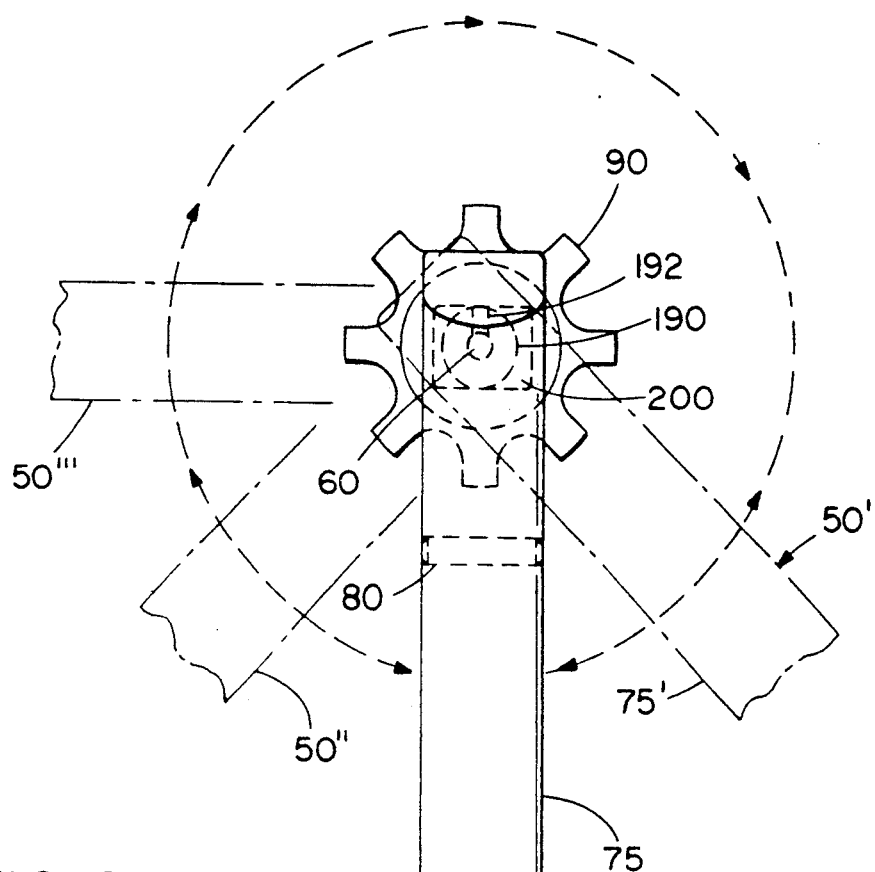
FIG. 8 is a rear elevation view of the instrument of FIG. 1b showing, in phantom, a few possible rotational positions for the actuating apparatus of the instrument.
Figure 8A:
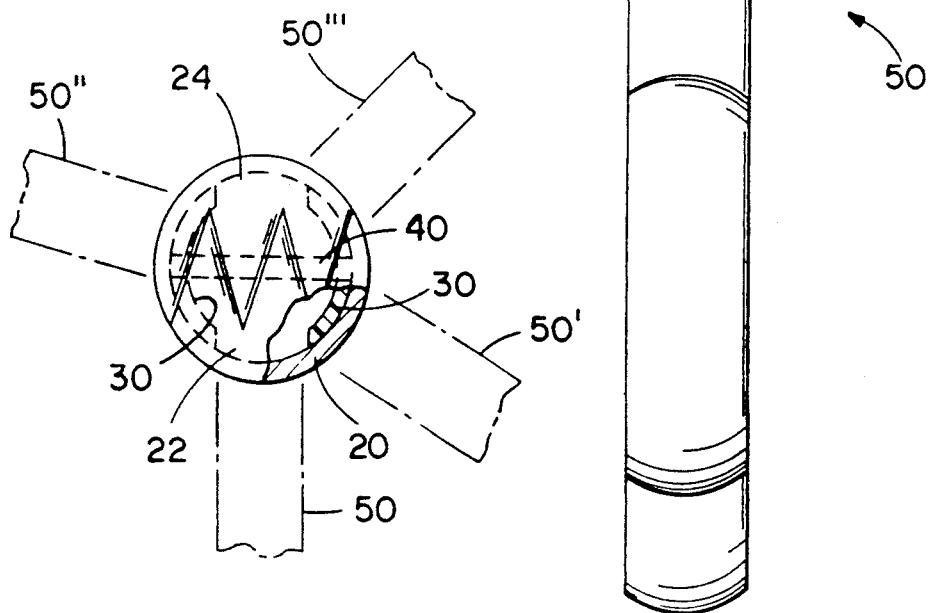
FIG. 8a is a front elevation view partly in section of the instrument shown in FIG. 8.

In operation, the pivotal movement of lever arm 75 as indicated at 70 in FIG. 1b causes the spherically surfaced element 190 to slidably bear against and contact the forward surface 230 of bore 200, or the rearward surface 240 of bore 200. In this manner, the engaged push rod 60 is moved backward and forward to impart the rotational motion to end effectors 22, 24 shown at 67, 68 in FIG. 1a. When it is desired to change the rotational orientation of the actuating mechanism 50 (comprising handle member 85 and pivotally engaged lever arm 75), the engaged arrangement of FIG. 1b (and also FIG. 9) is changed to the disengaged arrangement of FIG. 3. This is accomplished by moving sleeve member 90 away from the rearward end 23 of metal tube 20 (i.e., distally), toward the end effectors 22, 24, against the force exerted by resilient spring 103. As shown in FIG. 3, when sleeve member 90 is moved in that way, handle member 85 is disengaged from sleeve 90. With the handle member 85 in the disengaged position as shown, the actuating mechanism 50 (handle member 85 and pivoted lever arms 75) is rotatable about metal tube 20 (and vice versa) to any desired position (from 0+ to 360°) as indicated at 50'-50''' in FIGS. 8 and 8a. In a typical operation, with the third and fourth fingers of the practitioner's hand in handle ring 910 of handle member 85, and with the thumb in lever ring 914 of the lever 75, sleeve 90 is moved away (i.e., disengaged) from handle member 85 by use of the forefinger of the hand, and is rotated using the same finger. Once desired rotation is achieved, the forefinger releases the sleeve 90, and handle 85 once again is engaged with sleeve 90 due to the resilient force of spring 103. It will be appreciated, that if desired, movement of the sleeve 90 forward, and rotation thereof may be accomplished by slipping the thumb out of ring 914, and using the forefinger and thumb together. Of course, other fingers can also be used to effect forward movement and rotation. In fact, if desired, the tube 20 (and sleeve if desired) can be held in one hand, while the actuating mechanism 50 is rotated with the other hand to the desired position. Regardless of how rotation is effected, when the desired amount of rotation is obtained, sleeve 90 is released, and spring 103 forges sleeve 90 back into engagement with handle member 85 with the respective tooth-like elements and slots of the ring and the sleeve mating with each other. It will be appreciated that because only a finite number of tooth-like elements and slots are provided, the final locked position will not necessarily be exactly the rotation position which was obtained in the unengaged position. However, by providing numerous tooth-like elements and slots, fine resolution of final rotation position will be obtainable.

Figure 7A:
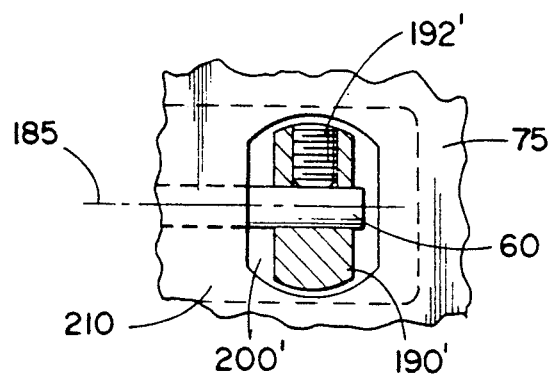
FIG. 7a is a partial plan view of a modification of the rod engaging element of FIG. 7.

Turning to FIG. 7a, an alternative embodiment of the push rod coupling element is seen. Coupling element 190' is shown as a truncated sphere as opposed to sphere element 190 of FIG. 7. Also, bore 200' is shown as a truncated sphere as opposed to the cylindrical transverse bore 200 of FIG. 7. It will be appreciated that the truncated spherical element 190' and the truncated spherical bore 200' can function appropriately, as the travel of lever arm 75 is most commonly 30° or less.

In a preferred embodiment shown in FIGS. 11a–h (which is alternative to the embodiments of FIGS. 7 and 7a), the push rod engaging element shown at 190" is essentially spherical and has a narrowed circumferential band 600. The radius of the band 600 is less than the radius, R, of the element 190" at its unnarrowed surfaces by an incremental distance L. The projection of the element 190" transverse to the band 600 has a radius of R-L as shown in FIG. 11b which can be received and closely fit and slid in a bore 200 of similar radius. As seen in FIG. 11b, the unnarrowed radius R of element 190" is greater than that of bore 200 so that only the narrowed band portion can be received in bore 200. As seen in FIGS. 11a–h generally spherical element 190" is provided with an axial diametrically located bore 191 for receiving push rod 60. As shown in FIGS. 11a and 11b, bore 191 is transverse to the narrowed circumferential band 600. A recessed radial set screw 192 passes through the narrow circumferential band 600 to intersect bore 191 for securing the push rod therein.

With reference to the side view of FIG. 11c, in assembly, the push rod coupling element 190" is first positioned with its narrowed circumferential, cylindrically shaped band portion 600 transverse to the longitudinal axis 207 of cylindrical bore 200 of lever arm 75 and element 190". The element 190" is advanced slot 210 in lever arm 75 as shown in FIG. 11d, with the width of band 600 being slightly wider than slot 210. With element 190" in the bridging position of FIG. 11d, the element 190" is rotated so that the circumferential band portion 600 is aligned with the longitudinal axis 207 of cylindrical bore 200 as shown in the front sectional view of FIG. 11e and the side view of FIG. 11f and with the diametrically axial bore 191 in element 190" aligned with slot 210. In this position, axial bore 191 receives the push rod 60 which is affixed to element 190" by radial set screw 192.

As seen best in FIG. 11g, the intersection of slot 210 with transverse cylindrical bore 200 partitions the bore and results in two circular spaced apart, opposed apertures 700, 701. Apertures 700, 701 slidably engage opposite surface portions of element 190" as shown, and restrain movement of element 190" along longitudinal axis 207 of bore 200 as the diameter (2R-2L) of the bore 200 and hence apertures 700, 701 is less than the diameter 2R of the unnarrowed, i.e. spherical portion of element 190". Thus, element 190" is free to rotate in bearing contact with apertures 700, 701 during reciprocal movement of push rod 60. As shown in FIG. 11a, the peripheral band 600 which permits insertion of element 190" into the bore 200, preferably subtends an arc "A" of about 20 to 65 degrees. The aforedescribed embodiment enables secure engagement of element 190" in handle 75 during all operational motions, e.g. back and forth motion of push rod 60 during movement of the end effectors, and rotational motion of push rod 60 relative to handle 75.

Typical dimensions for the preferred push rod engaging element of FIGS. 11a–h are as follows:

| | |
|---|---|
| Element 190" | brass sphere with radius R = .2 inch; |
| | width of band 600 = .15 inch; |
| | radius at band 600 = .1875 inch |
| | L = .0125 inch |
| | "A" = 50 degrees |
| Bore 200 | Diameter = .375 inch |
| Slot 210 | Width = .125 inch |
| Axial Bore 191 | Diameter = .1 inch |
| Set Screw 192 | Diameter = .138 inch |

Figure 9A:
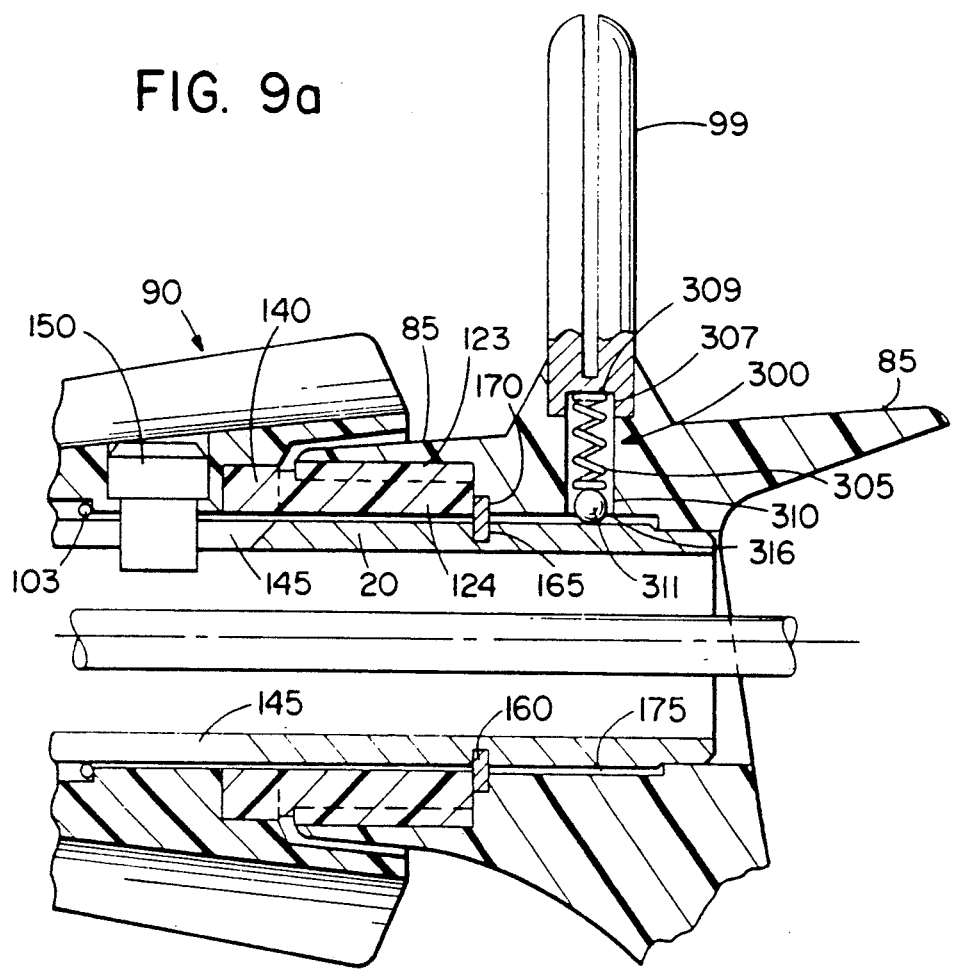
FIG. 9a is a side elevation view of a portion of the instrument of FIG. 1b.
Figure 9B:
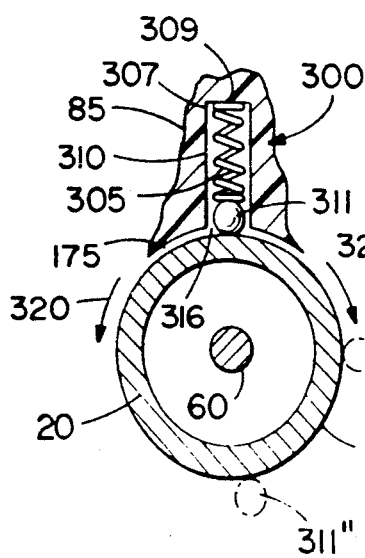

With reference to FIG. 9a which is an enlargement of a portion of FIG. 1b, and with reference to FIG. 9b, it is seen that the handle member 85 is provided with an outwardly extending electrode 99. Electrode 99 is adapted to receive electrical power for transmission to metal tube 20 and thence to end effectors 22, 24 (for cauterization procedures). In the prior art, the electrodes of the art are fixedly coupled to both the handle member and to the metal tube. However, in the present invention, because metal tube 20 can rotate relative to the handle member 85, an electrical contact arrangement 300 is utilized which ensures that power is not interrupted regardless of the rotational orientation of handle member 85. In particular, the electrical contact arrangement 300 comprises the electrode 99, a resilient metal spring element 305, and a metal contact element 311. The resilient metal spring element 305 is seated in a bore 310 in the handle member 85. The bore 310 is perpendicular to the longitudinal axis of the metal tube 20. Bore 310 includes a closed end 307 which forms the base 309 of electrode 99, and the resilient spring 305 bears against base 309. Because the resilient metal spring 305 is in compression, it is biased to urge the spherical metal contact 311, partially enclosed in bore 310, through a bore opening 316 and against the outer peripheral surface 313 of metal tube 20. With the aforedescribed arrangement, during rotation of handle member 85, as indicated at 320 and 321, metal element 311 will roll or slide along in contact with the outer periphery 313 of metal tube 20 such that continuous electrical contact between metal tube 20 and electrode 99 is maintained.

Figure 9D:
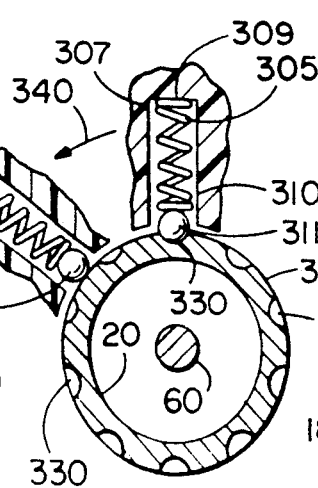
FIGS. 9d and 9e are respectively a cross sectional view and a side elevation view partially in section of an electrical contact arrangement according to the second embodiment of the invention of FIG. 9c.
Figure 9E:
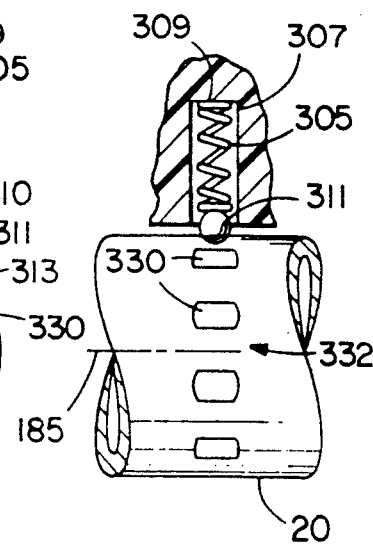
Figure 9C:
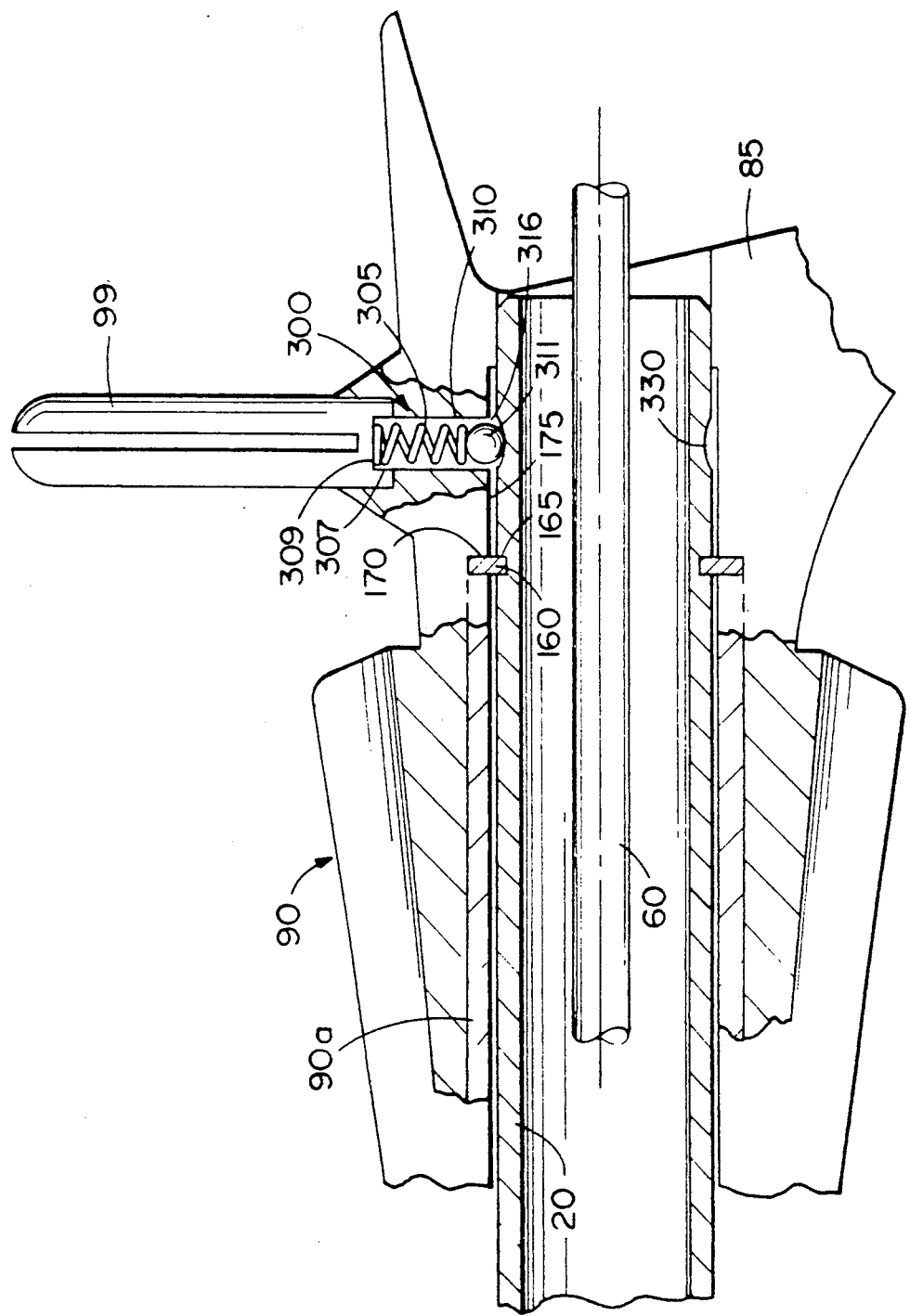
FIG. 9c is a side elevation view partly in section of a portion of a second embodiment of the invention which comprises an instrument similar to the instrument of FIG. 1b.

In a further embodiment of the present invention, illustrated in FIGS. 9c, 9d and 9e, a plurality of recesses, 330 (which can be open bottom slots) are provided in a row 332 around the circumference 313 of metal tube 20. The recesses 330 preferably have a shape generally conforming to that of contact element 311 so that the contact element 311 securely seats in a recess 330 until handle 85 is rotated, e.g. as indicated at 340 in FIG. 9d. When handle 85 is rotated, contact element 311 moves up out of a recess 330 and over the peripheral outer surface 313 of metal tube 20 to another recess 330 until rotation is discontinued. The recesses 330 are preferably evenly spaced about the periphery of metal tube 20 so that a preselected angular rotation can be established by travel of element 311 over a particular number of recesses 330. With the provided embodiment of FIGS. 9c, 9d and 9e, the entire sleeve arrangement of the instrument can be simplified as it is the contact element 311 in conjunction with spring 305 which keeps the handle 85 from rotating relative to the tube 20. In fact, as shown in FIG. 9c, neither sleeve 90, inner sleeve or ferrule 90a, nor handle 84 includes the teeth and slot arrangement of FIG. 9a. Also missing are the spring (103), the ring (124), etc. All that remains is the retaining ring 160 which prevents the handle (with the integral sleeve 90 and ferrule 90a which is fixed to sleeve 90) from sliding off of the tube 20, but which allows rotation of the handle 85 relative to the tube 20. It should be noted, that instead of using a retaining ring 160 and a ferrule and sleeve which are integral with the handle 85 as shown in FIG. 9c, a ferrule such as disclosed in parent application Ser. No. 07/680,392 can be utilized in conjunction with the step rotation mechanism of the electrode 99. It should also be recognized that instead of utilizing recesses or detents 330 in the metal tube 20 and a sphere 311 which rides in the detents, protrusions and alternately shaped contact elements could be utilized.

In accord with another aspect of the present invention, and as illustrated in FIGS 1b, 10, 10-1, and 10a–10i, improved ratchet mechanisms for endoscopic tools are provided. The improved ratchet mechanism, which can be used in conjunction with any medical tool and not just endoscopic tools enables end effectors 22, 24 to be locked in any of many positions (two such positions being shown in FIG. 10d) such that further movement of the end effectors toward each other is permitted, but further movement of the end effectors away from each other is not permitted except if the ratchet mechanism is purposely unlocked. Such a ratchet mechanism finds particular use in clamping devices, although it is not limited thereto.

In accord with the ratchet mechanism invention, the ratchet mechanism comprises a cantilevered resilient strip 400 with a locking barb 412, where the strip 400 is located on one of the handle 85 and lever 75 if the surgical instrument a ratchet element 499 located on the other of the handle 85 and lever 75 of the surgical instrument and having a plurality of teeth 419 radially displaced from a pivot 80 coupling the handle and lever, with each tooth 419 having an edge surface 498 on parallel axes which are parallel to the axis of the pivot 80, and a camming lever means 440 which in a first position forces the locking barb 412 into contact with the ratchet 499, and in a second position does not force the locking barb 412 into contact with the ratchet 499, wherein the barb 412 preferably also has an edge surface on an axis parallel to the axis of the pivot. The edge of the teeth 419 of the ratchet 499 are preferably located along an arc of a circle having its center point being the pivot 80 which couples the handle and the lever.

Figure 10:
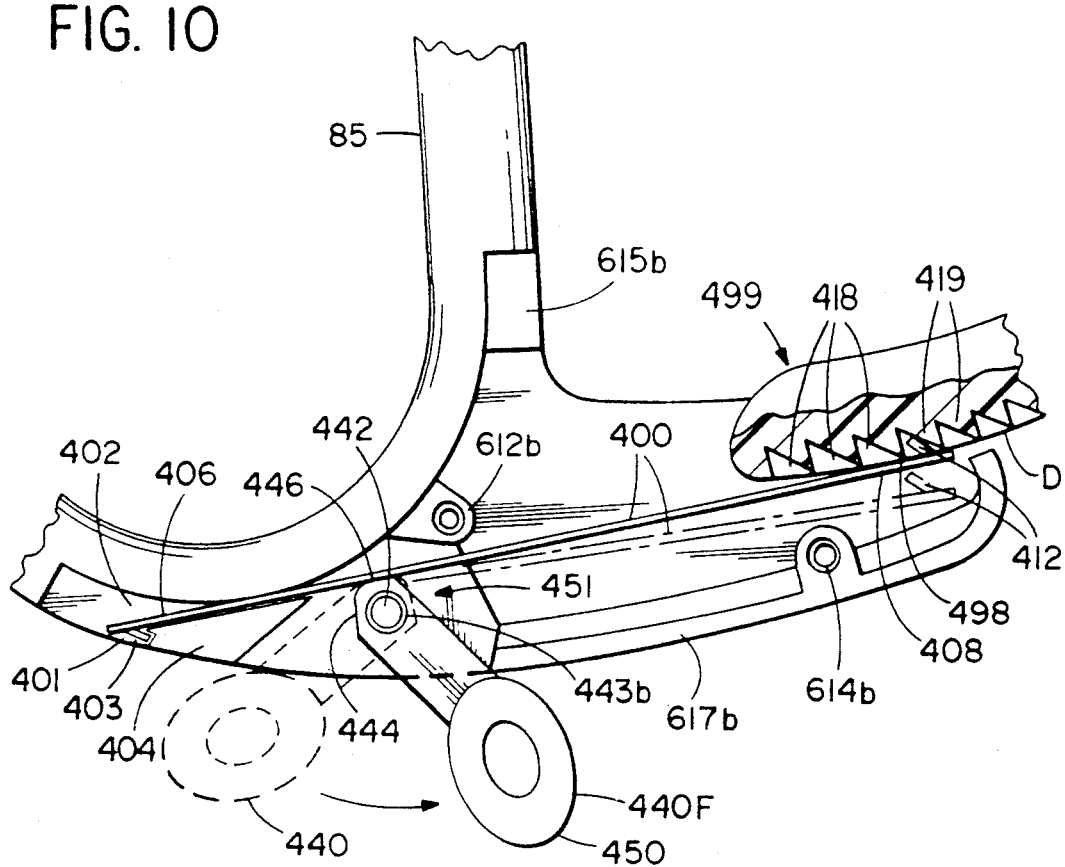
FIG. 10 is a partial side elevation view of the ratchet portion of the instrument of FIG. 1b.

In a first preferred embodiment of the ratchet mechanism of the invention, and with particular reference to FIGS. 1b and 10, the cantilevered resilient strip or leaf spring 400 (shown also in FIG. 10c) has a downwardly extending punched out barb 401 for fixing the resilient strip 400 in the handle 85 of the surgical instrument, and an upwardly extending barb or locking element 412 for mating with the ratchet 499 in the lever member 75. Locking element 412 is preferably punched out of the resilient strip 400 and preferably makes a forty-five degree angle relative thereto. Locking element 412 preferably has an edge surface 497 which is parallel to the axis of pivot 80. The resilient strip 400 is inserted into a slot 402 in handle member 85 with the downwardly extending barb 401 extending into slot 403 of the handle member 85. The resilient strip 400 is engaged in the handle member 85 at a first location by a fixing post or surface 404 which establishes a cantilever engagement at the end portion 406 of strip 400; i.e. end portion 408 of resilient strip 400 is a "free" end. Preferably, the fixing surface 404 is located substantially closer to barb 401 than to barb 412, and thereby provides a springy action. The springy action permits the teeth on the hereinafter described ratchet of the lever means to ride pass the barb in the direction of the barb such that further movement of the end effectors toward each other is permitted even after activation of the ratchet mechanism.

The leaf spring 400 is maintained in the handle 85 via use of a handle cover 610 (shown in FIGS. 10h and 10i) which includes several posts 612a, 614a which mate with post holes 612b and 614b on the handle 85 (seen in FIG. 10), and several mating surfaces 615a, 617a which mate with opposed surfaces or slots 615b, 617b on handle 85.

As seen in FIG. 1b, the resilient strip 400 is preferably positioned at the portion 410 of handle member 85 which extends furthest and is most remote from the pivotal engagement 80 of 400 extends at it free end portion 408 toward the portion 414 of the lever arm 75 which is most remote from pivotal engagement 80. By providing the ratchet mechanism at a distance from the point or pivotal engagement 80, finer resolution of possible locked positions is obtainable, as the arc segment for one degree of rotation is larger than an arc segment for one degree of rotation which would be located along an arc closer to the pivot point 80.

Figures 1, 10:
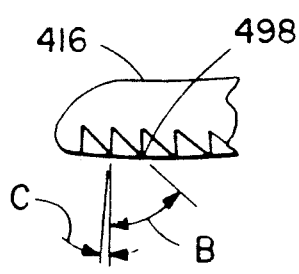
Figure 10A:
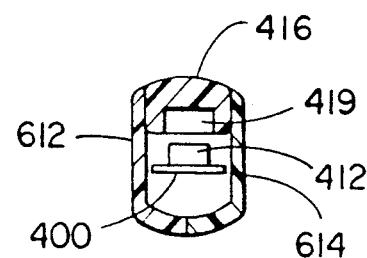
FIGS. 10a–10c show various details of the portion of the instrument shown in FIG. 10.
Figure 10B:
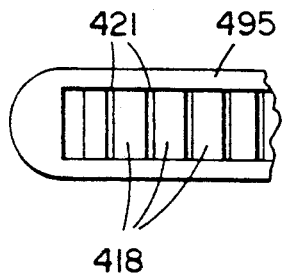
Figure 10C:
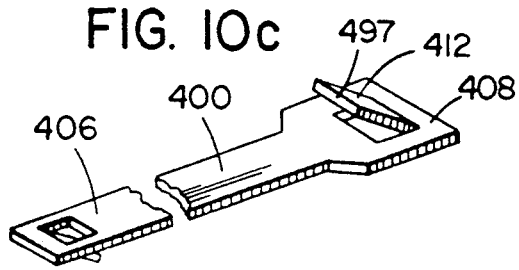
Figure 10D:
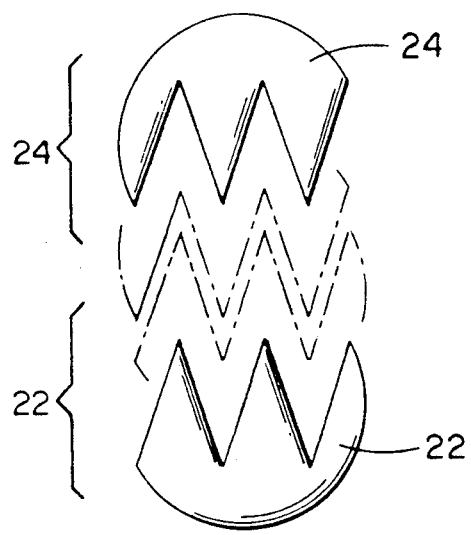

As aforementioned, the ratchet mechanism of the invention includes a ratchet 499 including teeth 419 and grooves 418 in the lever arm 75. As seen in FIGS. 1b and 10, an elongate arm 416 extends from lever arm 75 adjacent its remote portion 414. The elongate arm 416 includes the plurality of teeth 419 and grooves 418. In one preferred embodiment, a tandem array of teeth 419 are formed from the same material as the lever arm 75 in a recessed cutout fashion with the teeth traversing a portion of the width of elongate arm 416 (as seen in FIG. 10b), but with support edges 495 being kept intact. As shown in FIG. 10a, the width of the teeth 419 is just slightly wider than the width of the barb 412 to provide close lateral constraint for the locking barb 412. In a preferred embodiment, thirteen teeth are provided. The thirteen teeth traverse an arc of approximately seventeen degrees (i.e., one tooth every 1.3 degrees). Preferably, the teeth are angled (as shown in FIG. 10-1 by angle "B") at forty-five degrees relative to the radius defined by pivot point 80, and the back edge of the teeth are provided with a ten degree re-entry angle (as shown in FIG. 10-1 by angle "C") relative to the radius. Also, preferably the teeth edges 498 (and the bottom of elongate arm 416) are formed so that they are located on an arc D which has a curving radius based on the distance between the edges 498 of the teeth 418 and the pivot pin 80; i.e., the edges of the teeth are located along an arc having the pivot pin as its center point. This guarantees that the barb 412 of the resilient strip 400 can mate with each groove 418 of the ratchet 499, as rotation of lever 75 relative to handle 85 causes each tooth 419 to pass the barb 412 at the same relative height. With the teeth 419 at the provided angle B and preferably along the arc D, and with the barb 412 of the leaf spring 400 at a similar angle, when the barb 412 is mated into a groove 418 between the teeth 419 as hereinafter described, the teeth 419 can still ride pass the barb 412 in the direction of the barb such that further movement of the end effectors 22, 24 toward each other is obtained. However, movement in the opposite direction is not obtainable.

The third element of the ratchet mechanism is the camming lever or latching means pivot arm 440. The camming lever has an integral post 442 intermediate its trigger end 450 and its cammed bearing end 451. The post 442 fits into post cutout holes 443a and 443b on the handle 85 and the handle cover 610 (seen in FIG. 10h and 10i) and thereby fixes the camming lever bearing end 451 adjacent the resilient strip 400 at a location adjacently forward the leaf spring fixing surface 404 towards the free end of resilient strip 400. Bearing end 451 of camming lever 440 has two distinct intersecting planar bearing faces 444 and 446. With pivot arm 440 positioned as in FIG. 1b with bearing face 444 abutting resilient strip 400, the lever arm 75 and its transverse elongate arm 416 are freely movable with respect to resilient strip 400 and without barb 412 engaging the teeth 419 and grooves 418 of the transverse elongate arm 416. Upon advancing the camming lever 400 to the position 440F shown in FIG. 10, (e.g., via use of a pinky finger) the bearing face 446 is brought into coplanar abutting contact with resilient strip 400 thereby causing the strip 400 to be resiliently deformed with its locking barbed element 412 at its free end 408 in engagement with an oppositely located receiver element or groove 418 as illustrated in FIG. 10.

It will be appreciated that elongate arm 416 moves upon rotational movement of lever arm 75. As aforementioned, the elongate arm 416 is arranged so that the ratchet comprised of the teeth 418 and groove 419 is brought into a closely adjacent opposed relationship with the resilient strip 400. Either prior to moving the elongate transverse arm 416 adjacent the barb 412 of the leaf spring 400, or with lever arm 75 and its elongate transverse arm 416 in a desired position (which represents a desired position of end effectors 22, 24), the camming lever 440 may be advanced to the position 440F shown in FIG. 1a and FIG. 10 to lock the lever arm 75 relative to the handle 85 (and hence to lock the end effectors at a set position). The lever arm 75 and handle 85 may then be squeezed and moved closer together if desired, with the barb 412 riding over each tooth 419 and into another groove 418. Each locking position corresponds to a respective position of the end effector elements 22, 24 (two such positions being indicated in FIG. 10d). However, unless the camming lever is returned to position 440, barb 412 will not disengage from the ratchet 499 in the transverse arm 416 to permit the end effectors to move away from each other.

Figure 10E:
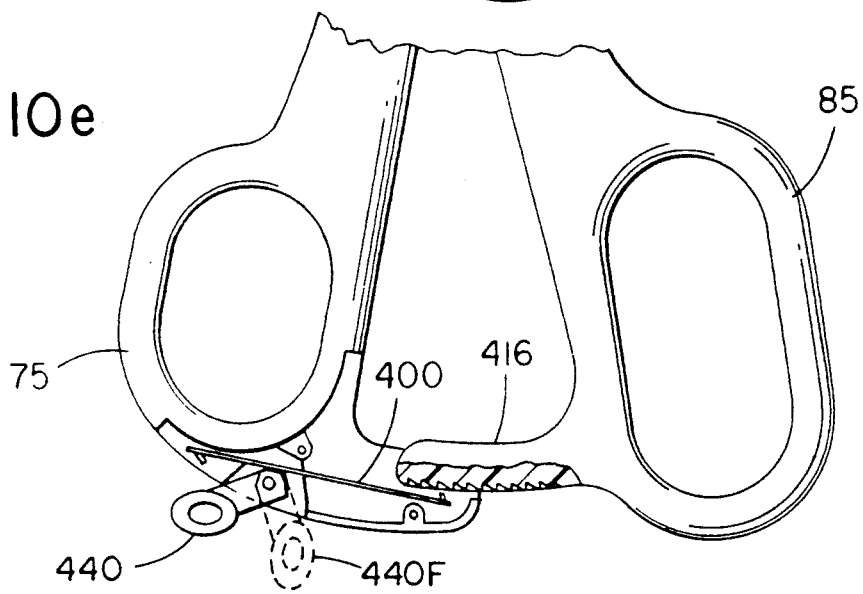
FIG. 10e shows an alternative embodiment to the configuration of FIG. 10.
Figure 10F:
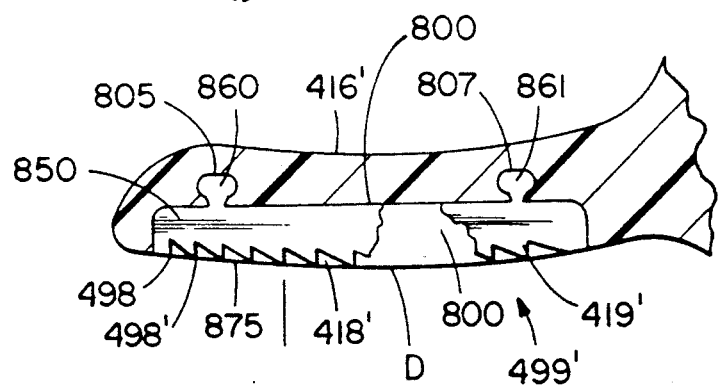
FIGS. 10f and 10g respectively show a fragmented side elevation view and a bottom plan view of an alternative embodiment of the teeth mechanism of FIG. 10.
Figure 10G:
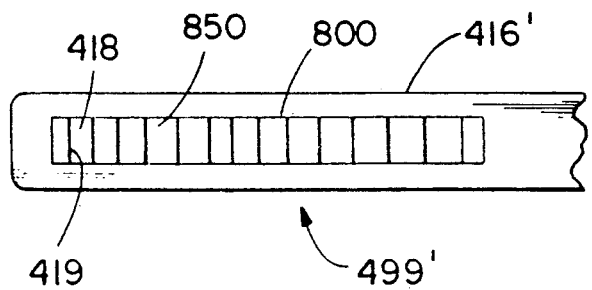
Figure 10H:
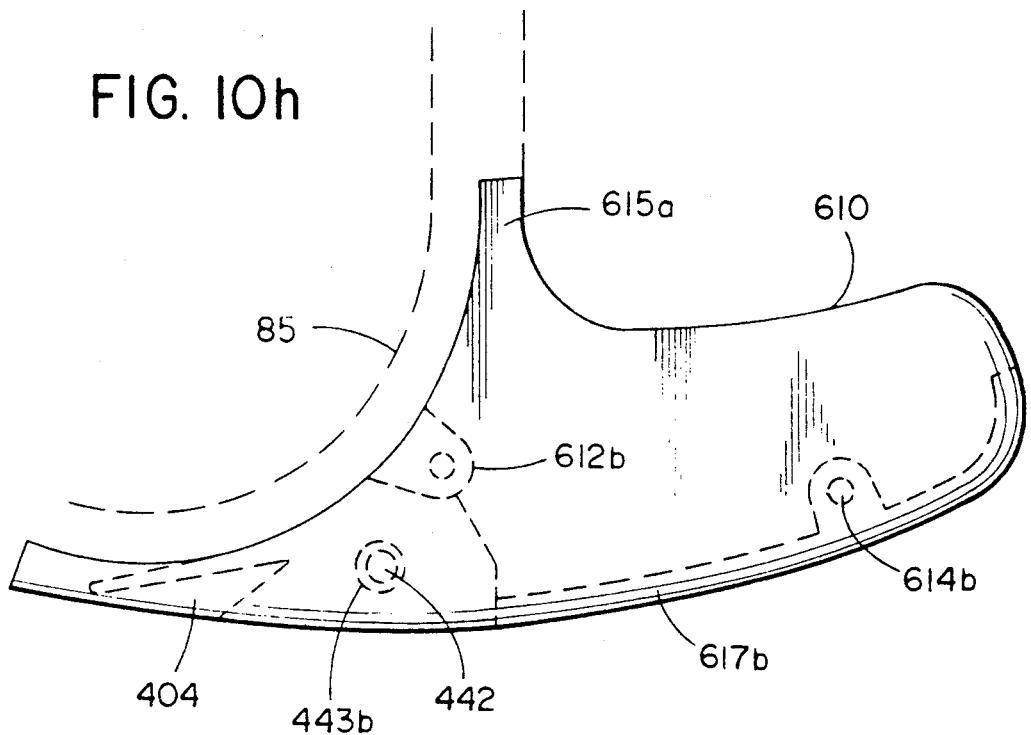
FIG. 10h is a side elevation view of a cover member for the ratchet housing portion of the handle of the instrument of FIG. 1b.
Figure 10I:
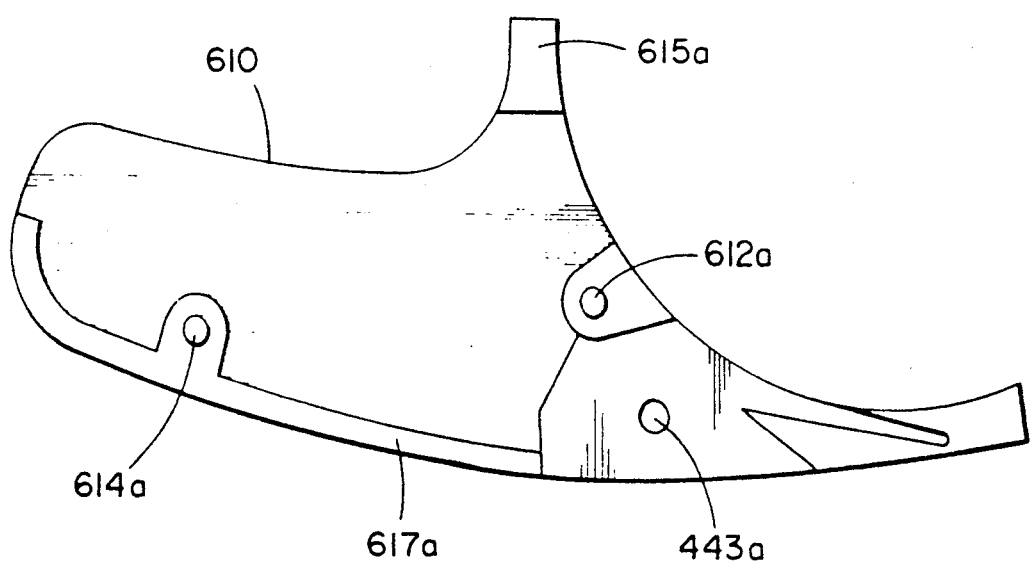
FIG. 10i is a side elevation view of the cover member of FIG. 10h showing the internal engaging elements thereof.

In a preferred embodiment of the present invention, shown in FIGS. 10f and 10g, the transverse elongate arm 416' of lever member 75, suitably made of molded plastic, is formed with an elongate open slot 800 extending along most of its length. The preformed slot 800 is formed with longitudinally spaced apart key ways 805, 807. A separately formed metal bar 850 is provided having a tandem array of integral toothlike elements 419' and grooves 418', and integral longitudinally spaced apart key elements 860, 861 on the side of metal bar 850 which is opposite to the toothlike members 419'. The metal bar 850 is inserted into slot 800 of elongate arm 416' to fit closely therein and securely engage elongate arm 416' by the forcible insertion of key elements 860, 861 into key ways 805, 807. When in position, the edges 498' of the toothlike members 419' of metal bar 850 are substantially coextensive with the outer edge 875 of elongate arm 416'. As with the teeth which are formed in the handle, the metal bar 850 is preferably formed with the teeth edges located in an arc D which has a curving radius based on the distance between the edges 498 of the teeth 419' and the pivot pin 80; i.e., the edges 498' of the teeth 419' are located along an arc D having the pivot pin as its center point. This guarantees that the barb 412 of the resilient strip 400 can mate with each groove 418' of the ratchet 499', as rotation of lever 75 relative to handle 85 causes each tooth 419' to pass the barb 412 at the same relative height.

While the hereinbefore described arrangement of FIG. 1b and FIG. 10 shows the preferred embodiment of the invention vis-a-vis the ratchet mechanism, if desired, and as shown in FIG. 10e, the resilient strip 400 can be engaged to the lever arm 75 instead of the handle member 85, and the elongate transverse arm 416 can be affixed to handle member 85 instead of elongate arm 416 (i.e., the parts are reversed). Also, while the elements of the preferred embodiment are located at the remote portions of lever arm 75 and handle member 85, they can be positioned instead at a location intermediate the pivotal engagement 80 and the remote extensions as indicated in phantom at 900 in FIG. 1b. In order to accommodate movement of the ratchet mechanism to such an intermediate location, it will be appreciated that the arc D' on the ratchet teeth will have to be of proportionally diminished radius. Also, because movement in degrees along the arc defines movement of the end effectors, if fine adjustment is required, then proportionally much finer teeth and grooves (and hence a finer barb) are required in the intermediate location than the preferred location. Additionally, in order to accommodate the ratchet mechanism, either the handles must be much wider so that the ratchet teeth, leaf spring, camming lever, etc. can be inserted in the handle and the lever without compromising the structural integrity of the handle and lever, or the ratchet mechanism must be moved out of the plane of the handle and lever. If the ratchet mechanism is moved out of the plane of the handle and lever, care must be taken to still provide an arrangement where the pivot point 80 is still the center of the arc for the ratchet teeth.

There have been illustrated and described herein endoscopic instruments having rotatable end effectors and having ratchet mechanisms. While particular embodiments of the invention have been described, it is not intended that the invention be limited thereto, as it is intended that the invention be as broad in scope as the art will allow and that the specification be read likewise. Thus, while particular materials were described as preferred, it will be appreciated that other materials could be utilized. For example, instead of a metal leaf spring for the ratchet mechanism, a hard plastic resilient strip could be utilized. Similarly, while certain dimensions and shapes of various objects such as the spherical rod-engaging member were disclosed as preferred, it will be appreciated that other shapes and dimensions can be utilized. For example, instead of having a sleeve having outside ribs running parallel to the longitudinal axis of the tube, the sleeve could have no ribs at all, or ribs running transverse the longitudinal axis. Further, while typical scissor-type handle elements were provided for both the lever arm and the handle, it will be appreciated that other arrangements such as plier handles, etc., could be utilized, provided relative movement between the two can be obtained to effect end effector pivoting. Thus, for example, the handle and/or lever arm could be some other type of gripping means. It will therefore be appreciated by those skilled in the art that yet other modifications could be made to the provided invention without deviating from its spirit and scope as so claimed.

We claim:

1. In a medical instrument having end effectors and a handle means and a lever arm means each coupled to at least one of said end effectors, said handle means and lever arm means being pivotably fixed relative to each other by a pivot means, wherein pivoting of said lever arm means relative to said handle means around said pivot means effects relative movement between said end effectors, an improvement comprising:

a releasable ratchet mechanism having a) a resilient member with opposite first and second opposite ends, said first end held in cantilever engagement with one of said handle means and said lever arm means, and with its second end extending away from said one of said handle means and said lever arm means with which said resilient member is in cantilever engagement toward the other of said handle means and said lever arm means, said resilient member having a locking element extending therefrom remote from its cantilevered engagement;

b) a ratchet means extending from said other of said handle means and lever arm means toward said cantilever engagement of said resilient member, said ratchet means being axially displaced relative to said locking element along an axis perpendicular to said pivot means but in closely adjacent opposed relationship to said locking element, said ratchet means having a plurality of teeth defining a plurality of grooves wherein each groove is adapted to individually receivably engage said locking element of said resilient member;

c) latching means movably coupled to said one of said handle means and lever arm means with which said resilient means is in cantilever engagement, said latching means for engaging and resiliently deforming said resilient member to cause engagement of said locking element in a groove of said ratchet means when said latching means is in a first position, and said latching means for either substantially disengaging said resilient means or for reducing the deformation of said resilient member when in a second position such that said locking means is substantially free from said ratchet means.

2. In a medical instrument according to claim 1, wherein:
said pivot means has a pivot axis;
said locking element has an extending edge surface on a second axis substantially parallel said pivot axis; and
said plurality of teeth have extending edge surfaces on third axes substantially parallel said second axis.

3. In a medical instrument according to claim 2, wherein:
said edge surfaces of said teeth of said ratchet means are located along an arc of a cylinder having said pivot axis as its center line.

4. In a medical instrument according to claim 1, wherein:
said resilient member comprises a leaf spring, and said locking element comprises a first punched out barb extending from said leaf spring.

5. In a medical instrument according to claim 4, wherein:
said punched out barb is at a substantially forty-five degree angle relative to said leaf spring.

6. In a medical instrument according to claim 1, wherein:
said resilient member comprises a leaf spring including an engaging means for fixedly engaging at its cantilevered end said one of said handle means and lever arm means with which said resilient means is in cantilever engagement.

7. In a medical instrument according to claim 1, wherein:
said handle means and said lever arm means comprise scissor type handle loop elements, and said resilient member is coupled to said one of said handle means and lever arm means and said ratchet means is coupled to the other of said handle means and lever arm means at locations on said loop elements remote from said pivot means.

8. In a medical instrument according to claim 1, wherein:
said handle means and lever arm means are comprised of plastic,
said ratchet means is formed as a unitary plastic component with the other of said handle means and said lever arm means, wit said teeth being formed in said ratchet means in a recessed cutout with the other of said handle means and said lever arm means, with said teeth being formed in said ratchet means in a recessed cutout fashion.

9. In a medical instrument according to claim 8, wherein:
said pivot means has a pivot axis,
said ratchet means has a first width along an axis parallel to said pivot axis, and
said teeth have a second width along said axis parallel to said pivot axis, wherein said second width is smaller than said first width.

10. In a medical instrument according to claim 1, wherein:
said handle means and lever arm means are comprised of plastic,
said ratchet means is a metal component in locked engagement with the other of said handle means and said lever arm means.

11. In a medical instrument according to claim 3, wherein:
each of said teeth have a first angled surface making an approximately forty-five degree angle relative to radii defining said arc.

12. In a medical instrument according to claim 11, wherein:
each of said teeth have a second angled surface making an approximately ten degree angle relative to said radii defining said arc 13. In a medical instrument according to claim 1, wherein:
said latching means comprises a camming lever means having a pivot pin pivotably engaging said one of said handle means and lever arm means with which said resilient means is in cantilever engagement, said camming lever having a bearing end adjacent said resilient means at a location toward said free end from where said resilient means is held in cantilever engagement, said bearing end having a first bearing surface, with said first bearing surface engaging and resiliently deforming said resilient member a first amount to cause engagement of said locking element in a groove of said ratchet means when said latching means is in said first position.

14. In a medical instrument according to claim 13, wherein:
said bearing end has a second bearing surface, with said second bearing surface resiliently deforming said resilient member a second amount when said locking means is in a second position, wherein said second amount can range from zero to an amount less than said first amount.

15. In a medical instrument according to claim 12, wherein:
said locking element is at a substantially forty-five degree angle relative to said resilient member such that when said latching means is in said first position with said locking element engaging said ratchet means, said handle means and said lever arm means can be squeezed together with said locking element riding on said first angled surface of respective teeth of said ratchet means and falling into grooves between said respective teeth.

16. In a medical instrument according to claim 3, wherein:
said resilient member comprises a leaf spring.

said locking element comprises a first punched out barb extending from said leaf spring at a substantially forty-five degree angle relative to said leaf spring, and said leaf spring further comprises a second punched out barb which fixedly engages said said one of said handle means and lever arm means with which said resilient means is in cantilever engagement at the cantilevered end of said leaf spring.

17. In a medical instrument according to claim 16, wherein:

said handle means and said lever arm means comprise scissor type handle loop elements, and said resilient member is coupled to said one of said handle means and lever arm means and said ratchet means is coupled to the other of said handle means and lever arm means at locations on said loop elements remote from said pivot means.

18. In a medical instrument according to claim 17, wherein:

said latching means comprises a camming )ever means having a pivot pin pivotably engaging said one of said handle means and lever arm means with which said resilient means is in cantilever engagement, said camming lever having a bearing end adjacent said resilient means at a location toward said free end from where said resilient means is held in cantilever engagement, said bearing end having a first bearing surface, with said first bearing surface engaging and resiliently deforming said resilient member a first amount to cause engagement of said locking element in a groove of said ratchet means when said latching means is in said first position.

19. In a medical instrument according to claim 1, wherein:

said medical instrument comprises an endoscopic instrument having a longitudinally extending hollow outer tube with a proximal end, a distal end, and a longitudinal axis, a push rod extending through said outer tube and having proximal and distal ends, an actuating means for imparting reciprocal axial motion to said push rod relative to said outer tube, said actuating means comprised of said handle means which engages said outer tube and said lever arm means which is coupled to said proximal end of said push rod, and said end effectors which are coupled to said push rod at said distal end of said push rod and pivotally coupled to said outer tube, whereby said reciprocal axial motion of said push rod is translated to pivotal movement of said end effectors.

20. In a medical instrument according to claim 17, wherein:

said medical instrument comprises an endoscopic instrument having a longitudinally extending hollow outer tube with a proximal end, a distal end, and a longitudinal axis, a push rod extending through said outer tube and having proximal and distal ends, an actuating means for imparting reciprocal axial motion to said push rod relative to said outer tube, said actuating means comprised of said handle means which engages said outer tube and said lever arm means which is coupled to said proximal end of said push rod, and said end effectors which are coupled to said push rod at said distal end of said push rod and pivotally coupled to said outer tube, whereby said reciprocal axial motion of said push rod is translated to pivotal movement of said end effectors.

21. A medical instrument, comprising:
a) a hollow outer tube having a proximal end, a distal end, and a longitudinal axis;
b) a push rod extending through said outer tube and having proximal and distal ends;
c) an actuating means for imparting reciprocal axial motion to said push rod relative to said outer tube, said actuating means comprising a handle means and a lever arm means, said handle means and lever arm means being coupled to each other by a pivot means, with said handle means engaging said outer tube, said lever arm means engaging said push rod;
d) end effector means coupled to said push rod at said distal end of said push rod and pivotally coupled to said outer tube, whereby pivoting of said lever arm means relative to said handle means around said pivot means is translated to pivotal movement of at least one of said end effectors; and
e) a releasable ratchet mechanism having
a resilient member engaged with and extending from a first of said handle means and said lever arm means, said resilient member having a locking element extending therefrom,
a ratchet means extending from the other of said handle means and said lever arm means said ratchet means being axially displaced relative to said locking element along an axis perpendicular to said pivot means but in closely adjacent opposed relationship to said locking element, said ratchet means having a plurality of teeth defining a plurality of grooves wherein each groove is adapted to individually receivably engage said locking element of said resilient member, and
latching means movably coupled to said first of said handle means and lever arm means, said latching means for engaging and resiliently deforming said resilient member to cause engagement of said locking element in a groove of said ratchet means when said latching means is in a first position.

22. A medical instrument according to claim 21, wherein:

said handle means and said lever arm means are pivotally engaged by said pivot means at a location adjacent said proximal end of said outer tube, and said handle means and lever arm means extend in an opposed relationship to respective remote ends which are at a substantially common distance away from said pivot means, and said resilient member engages said first of said handle means and said lever arm means at the remote end thereof.

23. A medical instrument according to claim 21, wherein:

said latching means comprises a pivot arm having a first end and a second end, said latching means being pivotally engaged between its first end and its second end to said first of said handle means and lever arm means, and said pivot arm having two distinct bearing faces at its second end which are alternatively positionable to abut said resilient member upon pivotal movement of said first end of said pivot arm, a first of said bearing face when abutting said resilient member causing said resilient member to deform and causing engagement of said locking element and said ratchet means, and the other of said bearing faces when abutting said resilient member enabling disengagement of said locking element from said ratchet means.

24. A medical instrument according to claim 21, wherein:
said pivot means has a pivot axis;
said locking element has an extending edge surface on a second axis substantially parallel said pivot axis; and
said plurality of teeth have extending edge surfaces on third axes substantially parallel said second axis.

25. A medical instrument according to claim 24, wherein:
said edge surfaces of said teeth of said ratchet means are located along an arc of a cylinder having said pivot axis as its center line.

26. A medical instrument according to claim 21, wherein:
said resilient member comprises a leaf spring, and said locking element comprises a first punched out barb extending from said leaf spring.

27. A medical instrument according to claim 26, wherein:
said punched out barb is at a substantially forty-five degree angle relative to said leaf spring.

28. A medical instrument according to claim 22, wherein:
said handle means and said lever arm means comprise scissor type handle loop elements, and said resilient member is coupled to said first of said handle means and lever arm means and said ratchet means is coupled to the other of said handle means and lever arm means.

29. A medical instrument according to claim 21, wherein:
said handle means and lever arm means are comprised of plastic,
said ratchet means is formed as a unitary plastic component with the other of said handle means and said lever arm means, with said teeth being formed in said ratchet means in a recessed cutout fashion.

30. A medical instrument according to claim 29, wherein:
said pivot means has a pivot axis,
said ratchet means has a first width along an axis parallel to said pivot axis, and
said teeth have a second width along said axis parallel to said pivot axis, wherein said second width is smaller than said first width.

31. A medical instrument according to claim 21, wherein:
said handle means and lever arm means are comprised of plastic,
said ratchet means is a metal component in locked engagement with the other of said handle means and said lever arm means.

32. A medical instrument according to claim 25, wherein:
each of said teeth have a first angled surface making an approximately forty-five degree angle relative to radii defining said arc.

33. A medical instrument according to claim 32, wherein:
each of said teeth have a second angled surface making an approximately ten degree angle relative to said radii defining said arc.

34. A medical instrument according to claim 33, wherein:
said locking element is at a substantially forty-five degree angle relative to said resilient member such that when said latching means is in a first position with said locking element engaging said ratchet means, said handle means and said lever arm means can be squeezed together with said locking element riding on said first angled surface of respective teeth of said ratchet means and falling into grooves between said respective teeth.

* * * * *